(12) United States Patent
Lentz

(10) Patent No.: US 6,824,543 B2
(45) Date of Patent: Nov. 30, 2004

(54) GUIDANCE SYSTEM FOR A CRYOCATHETER

(75) Inventor: David J. Lentz, La Jolla, CA (US)

(73) Assignee: CryoCor, Inc., San Diego, CA (US)

( * ) Notice: Subject to any disclaimer, the term of this patent is extended or adjusted under 35 U.S.C. 154(b) by 74 days.

(21) Appl. No.: 10/317,842

(22) Filed: Dec. 11, 2002

(65) Prior Publication Data

US 2004/0116915 A1 Jun. 17, 2004

(51) Int. Cl.$^7$ .............................................. A61B 18/18
(52) U.S. Cl. ...................... 606/21; 604/95.04; 604/533; 600/585
(58) Field of Search ...................... 606/20–26; 600/585; 604/95.04, 523, 528, 533

(56) References Cited

U.S. PATENT DOCUMENTS

| | | | |
|---|---|---|---|
| 4,838,268 A | | 6/1989 | Keith |
| 5,147,355 A | | 9/1992 | Friedman |
| 5,209,727 A | | 5/1993 | Radisch |
| 5,336,184 A | * | 8/1994 | Teirstein ............... 604/103.04 |
| 5,358,472 A | * | 10/1994 | Vance et al. ................... 604/22 |
| 5,490,859 A | | 2/1996 | Mische |
| 5,516,336 A | | 5/1996 | McInnes |
| 5,575,771 A | * | 11/1996 | Walinsky ................. 604/96.01 |
| 5,842,984 A | * | 12/1998 | Avitall ......................... 600/374 |
| 5,868,735 A | * | 2/1999 | Lafontaine .................... 606/21 |
| 6,012,457 A | | 1/2000 | Lesh |
| 6,024,740 A | | 2/2000 | Lesh |
| 6,126,649 A | * | 10/2000 | VanTassel et al. .......... 604/528 |
| 6,149,574 A | | 11/2000 | Trauthen |
| 6,237,355 B1 | | 5/2001 | Li |
| 6,245,064 B1 | | 6/2001 | Lesh |
| 6,562,030 B1 | | 5/2003 | Abboud et al. |
| 6,565,555 B1 | * | 5/2003 | Ryan et al. ................... 606/18 |
| 6,569,158 B1 | | 5/2003 | Abboud et al. |
| 6,575,933 B1 | | 6/2003 | Wittenberger et al. |
| 6,575,966 B2 | | 6/2003 | Lane et al. |
| 6,579,287 B2 | | 6/2003 | Wittenberger et al. |
| 6,585,717 B1 | | 7/2003 | Wittenberger et al. |
| 6,589,234 B2 | | 7/2003 | Lalonde et al. |
| 6,592,577 B2 | | 7/2003 | Abboud et al. |
| 6,595,988 B2 | | 7/2003 | Wittenberger et al. |
| 6,602,247 B2 | | 8/2003 | Lalonde |
| 6,629,972 B2 | | 10/2003 | Lehmann et al. |
| 6,635,053 B1 | | 10/2003 | Lalonde et al. |

\* cited by examiner

*Primary Examiner*—Michael Peffley
(74) *Attorney, Agent, or Firm*—Nydegger & Associates

(57) ABSTRACT

A system for guiding a cryocatheter through the vasculature of a patient includes a guidewire positioned in the vasculature across a predetermined site. A connector is attached to the distal end of the cryocatheter and is configured to receive the guidewire. The connector is then placed over the guidewire to guide the cryocatheter through the vasculature along the guidewire to the predetermined site. The tip of the cryocatheter can then be used at the predetermined site to cryoablate the tissue or otherwise remove heat from the predetermined site.

16 Claims, 3 Drawing Sheets

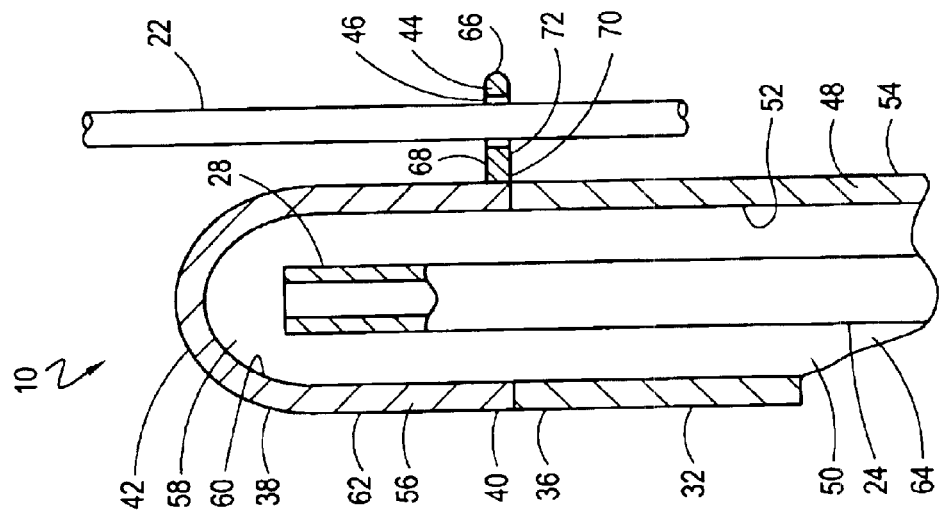
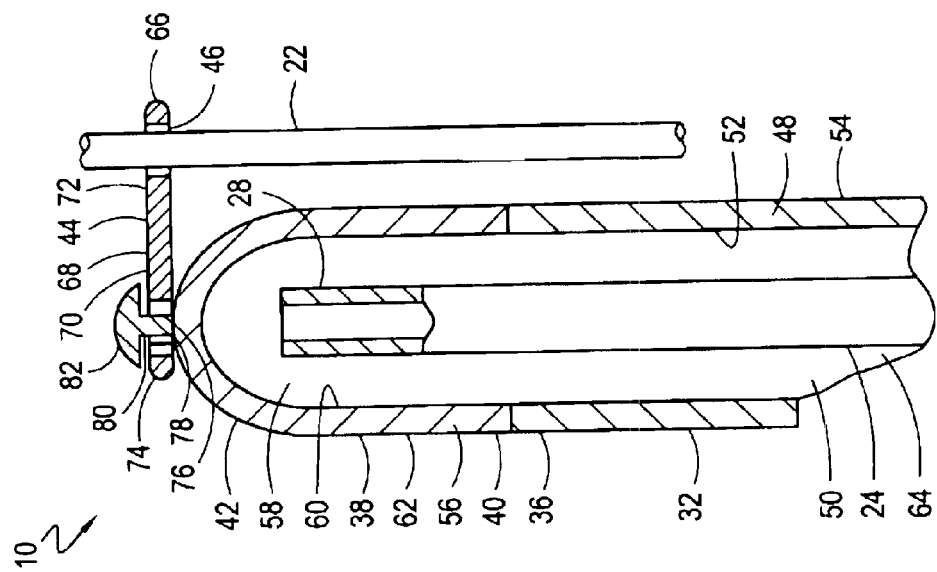
Fig. 3A
Fig. 3B

GUIDANCE SYSTEM FOR A CRYOCATHETER

FIELD OF THE INVENTION

The present invention pertains generally to devices and methods for guiding catheters through the vasculature of a patient. More particularly, the present invention pertains to devices and methods for positioning a catheter tip at a predetermined site in the vasculature of a patient. The present invention is particularly, but not exclusively, useful for positioning the tip of a cardiac cryoablation catheter at a predetermined site in the vasculature for surgical procedures requiring effective heat transfer.

BACKGROUND OF THE INVENTION

Guidance and positioning mechanisms are important considerations in the manufacture and operation of an invasive catheter. Specifically, the ability to easily and accurately guide the catheter through a patient's vasculature to a target site is an essential catheter characteristic. Once the catheter is near the target site, the ability to then accurately position the catheter tip at the target site is also important.

Several devices have been previously suggested for the purpose of steering a catheter through the vasculature of a patient For example, U.S. Pat. No. 1,060,665, which issued to Bell on May 6,1913 for an invention entitled "Catheter", incorporates a pre-bent stiffening member located at the catheter's distal end for use of the member's bending bias in steering the catheter through the vasculature. Recently, more complex devices have relied on a pull-wire to deflect the catheter tip. In general, these mechanisms have included concentric or eccentric pull-wires that generate an eccentrically applied force on the tip of the catheter. For example, U.S. Pat. No. 4,456,017, which issued to Miles for an invention entitled "Coil Spring Guide with Deflectable Tip," incorporates a concentric core wire for this purpose. In contrast, U.S. Pat. No. 4,586,923, which issued to Gould et al., uses an eccentric wire for the same purpose. Furthermore, devices have also been proposed which will bias the deflection of a catheter tip in a predetermined plane. An example of such a device is disclosed in U.S. Pat. No. 4,886,067, which issued to Palermo for an invention entitled "steerable Guidewire with a Soft Adjustable Tip." In the Palermo patent, such a bias is established by flattening the core wire. Another device that is often used for steering a catheter through the vasculature of a patient involves a guidewire that is pre-positioned in the vasculature across a target site. The catheter is then engaged with the guidewire, and is advanced over the guidewire through the vasculature to the target site.

At the target site, some surgical applications require that the tip of the catheter be accurately positioned. In particular, for cryoablation procedures, the tip of a cryoablation catheter must be accurately positioned to contact tissue at the target site for cryoablating the tissue. Importantly, a cryoablation catheter has unique structural aspects and thermodynamic properties that must be considered in the design of its guidance and positioning mechanism. Specifically, a cryoablation catheter is typically designed with a closed tip portion that forms an expansion chamber. In operation, a cryogenic fluid is introduced into the expansion chamber through a supply line to rapidly cool the tip portion. Consequently, tissue in contact with the tip portion at the target site is cryoablated. Importantly, whatever guidance mechanism may be used to position the tip portion in the vasculature, it must not interfere with the intended operation of the cryoablation catheter.

Prior art mechanisms for guiding and positioning a catheter generally have not been designed to accommodate the particular structural aspects required for the catheter's intended application. Accordingly, they have not specifically considered the requirements for operation of a cryoablation catheter. For instance, existing over-the-wire guiding mechanisms that pass a guidewire through the catheter tip cannot be used with a cryoablation catheter because the required closed tip portion of a cryoablation catheter prevents the guidewire from fully extending through the catheter. In any event, the guidewire must not compromise the expansion chamber or interfere with the flow of cryogenic fluid to and from the expansion chamber.

In light of the above, it is an object of the present invention to provide a device and method for advancing a catheter through a patient's vasculature and for positioning the catheter tip at a predetermined site in the patient. Another object of the present invention is to provide a device and method for guiding a cryoablation catheter through a patient's vasculature without compromising the expansion chamber in the catheter tip. Still another object of the present invention is to provide a device and method for guiding and positioning a catheter in the vasculature of a patient that is relatively easy to manufacture, is simple to use, and is comparatively cost effective.

SUMMARY OF THE INVENTION

The present invention is directed to a system and method for guiding a cryocatheter through the vasculature of a patient to position the distal end of the cryocatheter at a predetermined site in the vasculature. As intended for the present invention, the system includes a connector that is incorporated with the distal end of the cryocatheter and is formed with a passageway configured to receive a guidewire. The guidewire is pre-positioned in the vasculature of the patient and leads to the predetermined site. When the connector is engaged with the guidewire, the cryocatheter can be advanced along the guidewire and through the vasculature to position the distal end of the cryocatheter at the predetermined site.

In detail, the cryocatheter includes a catheter and a tip. The catheter has a proximal end and a distal end, and is formed with a wall surrounding a lumen that extends between the proximal and distal ends of the catheter. The tip has a closed distal end and an open proximal end, and is formed with a wall surrounding a chamber. Structurally, the open proximal end of the tip is attached to the distal end of the catheter so that the chamber formed by the tip is in fluid communication with the lumen of the catheter. Preferably, the tip is substantially cylindrical-shaped and defines a longitudinal axis.

The system of the present invention further includes a tubular-shaped supply line that has a proximal end and a distal end. The supply line is positioned in the lumen of the catheter with its distal end located in the chamber. With this structure, in addition to the supply line, a fluid return lumen is established inside the catheter between the supply line and the inner wall of the catheter. Furthermore, the proximal end of the supply line is connected to a fluid supply, which is in fluid communication with the chamber through the supply line.

As indicated above, the present invention envisions a connector that is operationally associated with the tip of the catheter. In one embodiment of the present invention, this connector is an eyelet. For this embodiment, the eyelet has an annular shaped member that is formed with a passageway for receiving the guidewire. Additionally, the eyelet has an extension arm with one end attached to the annular shaped member. In one variation of this embodiment, the other end of the extension arm is fixedly attached directly to the tip.

In a variation of the "eyelet" embodiment for the present invention, the system also includes a post that extends axially from the closed end of the tip in a distal direction. For this embodiment, a ring is formed at the end of the extension arm opposite the annular shaped member and is configured to surround the post. Additionally, a cap is attached to the distal end of the post to hold the ring on the post, to thereby allow the annular shaped member of the connector to rotate (swivel) around the longitudinal axis.

In still another embodiment of the present invention, the connector is formed into the wall of the tip. Structurally, for this embodiment of the present invention, the connector is a passageway that is formed between the inner and outer surfaces of the tip wall. More specifically, the passageway extends between a first opening and a second opening, which are located on the outer surface of the tip wall. In yet another embodiment of the present invention, the connector is formed into the wall of the catheter. For this embodiment, the connector is a passageway that is formed between the inner and outer surfaces of the catheter wall. The passageway extends between a first opening and a second opening, which are located on the outer surface of the catheter wall. Importantly, in either case, the passageway should not compromise the expansion chamber or reduce the efficacy of the thermodynamic structure of the tip.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is a cross-sectional view of the catheter tip and the connector as seen along the line 3—3 in FIG. 2;

FIG. 3B is a cross-sectional view of the catheter tip, in combination with an alternate embodiment for the connector, as the combination would be seen along the line 3—3 in FIG. 2;

DESCRIPTION OF THE PREFERRED EMBODIMENTS

Figure 1:
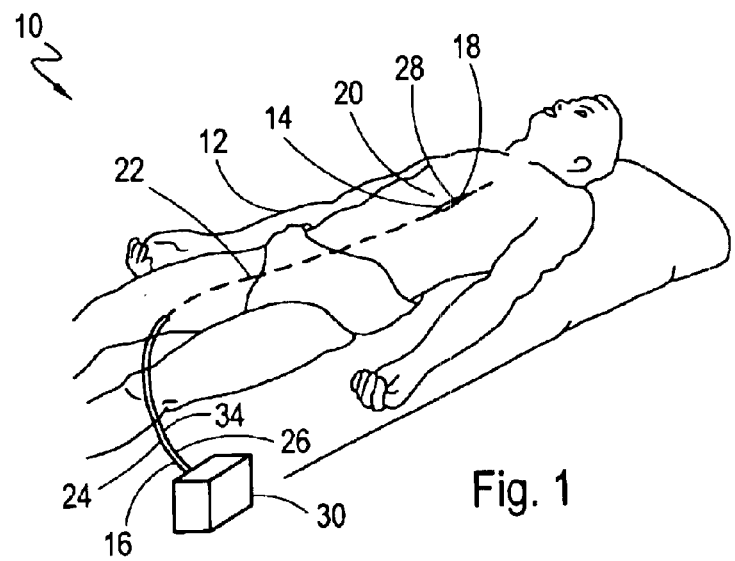
FIG. 1 is a perspective view of a system according to the present invention positioned in the vasculature of a patient.

Referring initially to FIG. 1, a catheter system in accordance with the present invention is shown and is generally designated 10. In FIG. 1, the system 10 of the present invention is shown positioned in the vasculature of a patient 12. As shown, the system 10 includes a cryocatheter 14 that has a proximal end 16 and a distal end 18. Also, as shown, the cryocatheter 14 is positioned at a predetermined site 20 in the vasculature of the patient 12. The system 10 also includes a guidewire 22 that is positioned in the vasculature of the patient 12 and extends past the predetermined site 20. Furthermore, the catheter system 10 includes a supply line 24 that has a proximal end 26 and a distal end 28. The supply line 24 is positioned in the cryocatheter 14 with the distal end 28 of the supply line 24 positioned at the distal end 18 of the cryocatheter 14. The proximal end 26 of the supply line 24 is connected to a fluid source 30.

Figure 2:
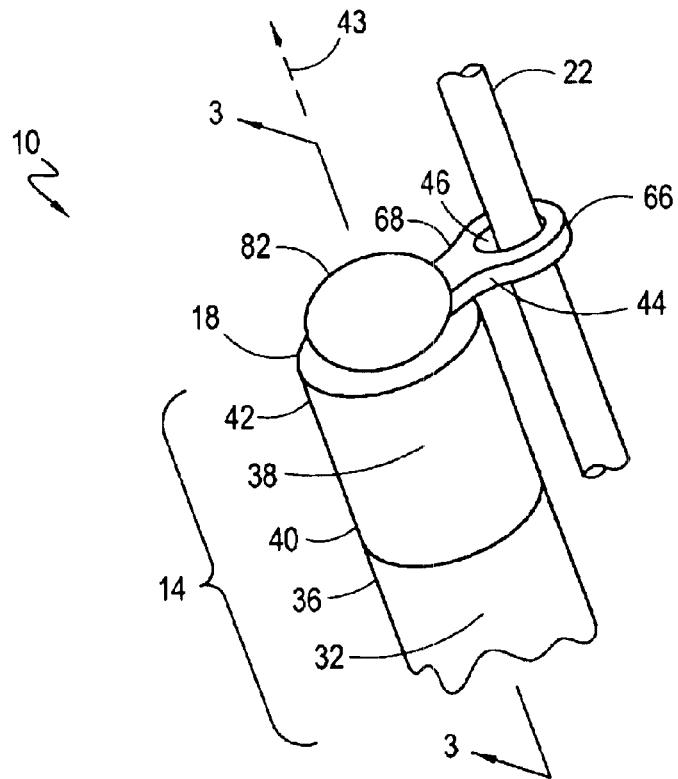
FIG. 2 is a perspective view of the catheter tip, shown in combination with one type embodiment of the connector, in accordance with the present invention.

Referring now to FIG. 2, the cryocatheter 14 includes a catheter body 32 that has a proximal end 34 (FIG. 1) and a distal end 36. The cryocatheter 14 also includes a tip 38 that has an open proximal end 40 and a closed distal end 42. Preferably, the tip 38 has a substantially cylindrical shape that defines a longitudinal axis 43. In any case, the proximal end 40 of the tip 38 is attached to the distal end 36 of the catheter body 32. Preferably, the tip 38 is made of a thermally conductive material, and the catheter body 32 is made of a thermally insulating material. Stated differently, the tip 38 conducts heat more effectively than the catheter body 32. The system 10 also includes a connector 44 that is attached to the distal end 18 of the cryocatheter 14. As shown, the connector 44 is formed with a passageway 46 for receiving the guidewire 22. Preferably, the guidewire 22 is a thin elongated rod with a circular cross-section. As will be appreciated by the skilled artisan, the guidewire 22 is flexible enough to pass through the vasculature of the patient 12 and is appropriately dimensioned to pass through the passageway 46 of the connector 44.

As shown in FIG. 3A, the catheter body 32 has a wall 48 that surrounds a lumen 50. As envisioned for the present invention, the lumen 50 extends between the proximal end 34 (FIG. 1) and the distal end 36 of the catheter body 32. Additionally, the wall 48 of the catheter body 32 has an inner surface 52 and an outer surface 54. Preferably, the catheter body 32 is a hollow, substantially cylindrical-shaped tube.

Still referring to FIG. 3A, it can be seen that the tip 38 of the cryocatheter 14 has a wall 56 surrounding an expansion chamber 58. The proximal end 40 of the tip 38 provides for fluid access to the expansion chamber 58, and the closed distal end 42 of the tip 38 partially encloses the expansion chamber 58. Furthermore, the wall 56 of the tip 38 has an inner surface 60 and an outer surface 62. Structurally, the proximal end 40 of the tip 38 is tightly affixed in a fluid-tight seal to the distal end 36 of the catheter body 32. Thus, the expansion chamber 58 is in fluid communication with the lumen 50 of the catheter body 32.

Still referring to FIG. 3A, it can be seen that the supply line 24 is positioned in the lumen 50 of the catheter body 32 with the distal end 28 of the supply line 24 positioned in the expansion chamber 58 of the tip 38. With this structure, the supply line 24 establishes fluid communication between the fluid source 30 and the expansion chamber 58 of the tip 38. Preferably, the supply line 24 is a hollow, substantially cylindrical-shaped tube. Structurally, the supply line 24 and the catheter body 32 form a fluid return 64 in the lumen 50 of the catheter body 32 between the supply line 24 and the inner surface 52 of the wall 48 of the catheter body 32.

A preferred embodiment of the present invention can be described with reference to FIGS. 2 and 3A. In this embodiment, the connector 44 is formed as a swivel to allow the connector 44 to rotate around the longitudinal axis 43. More specifically, the connector 44 includes an annular shaped member 66 and an extension arm 68. The annular shaped member 66 is formed to surround the passageway 46 for receiving the guidewire 22 through the passageway 46 to connect the cryocatheter 14 with the guidewire 22. As shown in FIG. 3A, the extension arm 68 has a first end 70 and a second end 72. For this embodiment, the first end 70 of the extension arm 68 is formed as a ring 74 and the second end 72 of the extension arm 68 is connected to the annular shaped member 66. The ring 74 is dimensioned to surround a post 76 that is attached to the tip 38. More specifically, the post 76 has a proximal end 78 and a distal end 80. The proximal end 78 of the post 76 is attached to the distal end 42 of tip 38 to extend the post 76 axially away from the tip 38 in a distal direction. A cap 82 is attached to a distal end 80 of the post 76 and is dimensioned to hold the ring 74 on the post 76 and to allow the connector 44 to rotate around the longitudinal axis 43.

In another embodiment of the present invention (see FIG. 3B), the first end 70 of the extension arm 68 is fixedly attached to the tip 38 of the cryocatheter 14 to extend its second end 72 radially outward from the longitudinal axis 43. Preferably, the first end 70 is attached to the proximal end 40 of the tip 38 near the distal end 36 of the catheter body 32. As with the previously disclosed embodiment, the connector 44 has an annular shaped member 66 that is connected to the second end 72 of the extension arm 68. Also, as with the other embodiment, the annular shaped member 66 is formed with the passageway 46 for receiving the guidewire 22.

Figure 3D:
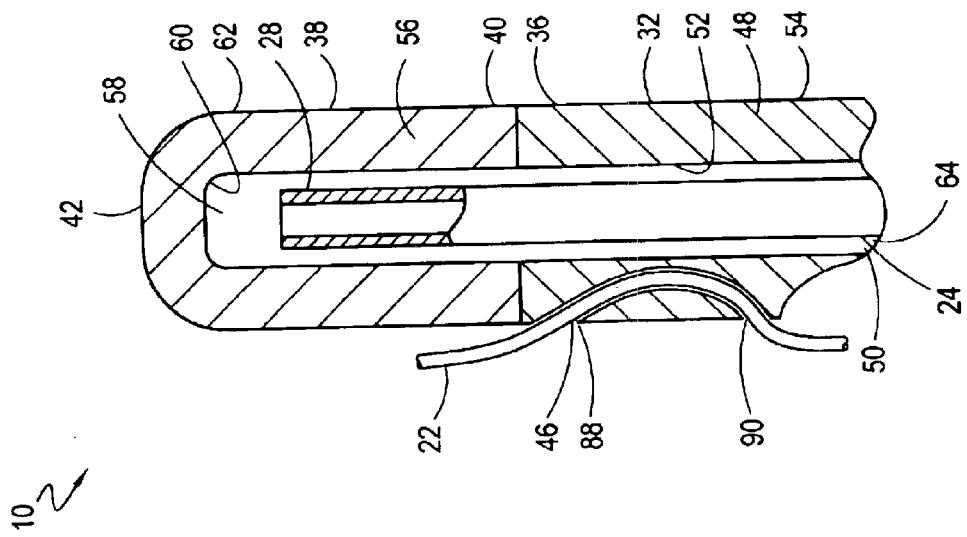
FIG. 3D is a cross-sectional view of a catheter tip, in combination with yet another alternate embodiment for the connector, as this combination would be seen along the line 3—3 in FIG. 2.
Figure 3C:
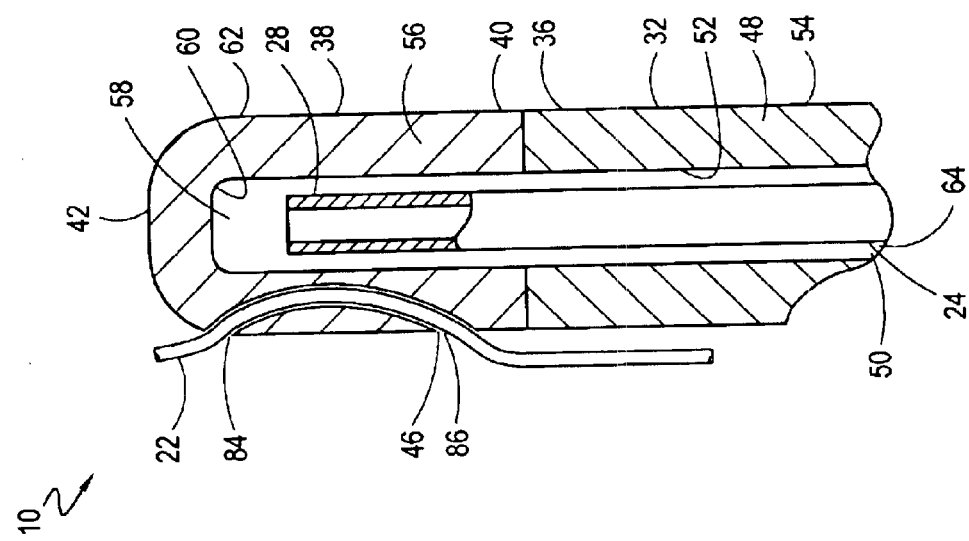
FIG. 3C is a cross-sectional view of a catheter tip, in combination with another alternate embodiment for the connector, as this combination would be seen along the line 3—3 in FIG. 2.

Still another embodiment of the present invention is shown in FIG. 3C. In this embodiment, the passageway 46 of the connector 44 is formed into the wall 56 of the tip 38. In this case, the passageway 46 is formed between the inner surface 60 and the outer surface 62 of the wall 56. As shown, the outer surface 62 of the wall 56 has a first opening 84 and a second opening 86. Structurally, the passageway 46 extends between the first opening 84 and the second opening 86 of the wall 48 to receive the guidewire 22 through the passageway 46. Preferably, the passageway 46 forms a slightly curved path through the wall 48 of the tip 38.

Another embodiment of the connector 44 is shown in FIG. 3D. In this embodiment, the passageway 46 of the connector 44 is formed into the wall 48 of the catheter body 32 substantially between the inner surface 52 and the outer surface 54 of the wall 48. As shown, the outer surface 54 of the wall 48 has a first opening 88 and a second opening 90. Structurally, the passageway 46 extends between the first opening 88 and the second opening 90 of the wall 48 to receive the guidewire 22. Preferably, the passageway 46 forms a slightly curved path through the wall 48 of the catheter body 32.

The operation of the system 10 can perhaps be best described with reference to FIGS. 1 and 3A. Initially, the guidewire 22 is pre-positioned in the vasculature of the patient 12 to extend past the predetermined site 20. The guidewire 22 is then threaded through the passageway 46 of the connector 44 to engage the cryocatheter 14 with the guidewire 22. With the guidewire 22 positioned through the passageway 46 of the connector 44, the distal end 18 of the cryocatheter 14 is advanced along the guidewire 22 through the vasculature of the patient 12 to position the tip 38 of the cryocatheter 14 at the predetermined site 20. The tip 38 of the cryocatheter 14 can then be manipulated as necessary. For example, the tip 38 can be engaged with other devices at the predetermined site 20, or it can be placed into contact with target tissue to perform a surgical cryoablation procedure on the target tissue. In any event, the supply line 24 introduces a cooled fluid from the fluid source 30 into the expansion chamber 58 of the tip 38. Inside the expansion chamber 58, the cooled fluid undergoes endothermic expansion to absorb heat from the tip 38 as the cooled fluid is transformed into a gas inside the expansion chamber 58. The gas is then removed from the chamber 58 through the fluid return 64 to allow the supply line 24 to introduce additional cooled fluid into the chamber 58. Once a procedure has been completed at the predetermined site 20, the cryocatheter 14 can be withdrawn from the vasculature over the guidewire 22.

While the particular catheter system and method as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system comprising:
    a guidewire adapted to be positioned across a predetermined site in the vasculature of a patient;
    a catheter body having a proximal end and a distal end, with a lumen formed therebetween;
    a tip attached to said distal end of said catheter body, wherein said tip is substantially cylindrical shaped and surrounds a chamber defining a longitudinal axis, said tip having an open end and a closed end, with said open end attached to said distal end of said catheter for fluid communication therewith;
    a connector positioned at said tip, said connector being formed with a passageway for receiving said guidewire therethrough, to advance said catheter body along said guidewire through the vasculature to position said tip at said predetermined site;
    a fluid source; and
    a hollow, tubular-shaped supply line having a proximal end and a distal end, said supply line being positioned inside said catheter body with said distal end thereof positioned in said chamber, and with said proximal end thereof coupled in fluid communication with said fluid source for introducing a fluid from said fluid source into said chamber through said supply line to cool said tip.

2. A system as recited in claim 1 wherein said connector is an eyelet comprising:
    an annular shaped member, with said annular shaped member defining said passageway; and
    an extension arm having a first end and a second end, wherein said first end of said extension arm is positioned at said tip and said second end of said extension arm is affixed to said annular shaped member to project said annular shaped member radially outward from said tip to receive said guidewire.

3. A system as recited in claim 2 wherein said first end of said extension arm is affixed to said tip at said open end thereof.

4. A system as recited in claim 2 wherein said first end of said extension arm is formed as a ring, and said system further comprises:
    a post having a proximal end and a distal end with said proximal end of said post attached to said closed end of said tip to extend said post axially from said tip in a distal direction to receive said ring around said post; and a cap attached to said distal end of said post for holding said connector on said tip for rotation around said axis.

5. A system as recited in claim 1 wherein said tip has a wall with an inner surface and an outer surface, and wherein said passageway extends through said wall between said inner surface and said outer surface from a first opening to a second opening, and wherein said first opening and said second opening are located on said outer surface of said wall of said tip.

6. A system as recited in claim 5, wherein said passageway extends from said first opening to said second opening along a substantially straight path.

7. A system as recited in claim 5, wherein said tip is made of a thermally conductive material and said catheter is made of a thermally insulating material.

8. A system as recited in claim 1, wherein said catheter body is substantially cylindrical-shaped and has a wall surrounding said lumen, with said wall having an inner surface and an outer surface, wherein said passageway extends through said wall between said inner surface and said outer surface from a first opening to a second opening, and wherein said first opening and said second opening are located on said outer surface of said wall.

9. A device comprising:
   a hollow tubular-shaped catheter body having a proximal end and a distal end;
   a cylindrical-shaped tip defining a longitudinal axis and having an open proximal end and a closed distal end to establish a chamber therebetween, wherein said proximal end of said tip is attached to said distal end of said catheter body for fluid communication therebetween;
   a connector positioned at said distal end of said catheter body and formed with a passageway for receiving the guidewire therethrough, to advance said catheter body through the vasculature of a patient and position said tip at the predetermined site therein; and
   a supply line having a hollow tubular shape with a proximal end and a distal end, said supply line being positioned inside said catheter body with said distal end thereof positioned in said chamber, and with said proximal end thereof coupled in fluid communication with a fluid source for introducing a fluid from said fluid source into said chamber through said supply line to cool said tip with the fluid.

10. A device as recited in claim 9 wherein said catheter body has a wall surrounding a lumen, with said wall having an inner surface and an outer surface, wherein said passageway extends through said wall from a first opening to a second opening, and wherein said first opening and said second opening are on said outer surface of said wail.

11. A device as recited in claim 10, wherein said passageway extends from said first opening to said second opening along a substantially curvilinear path.

12. A method for positioning a tip of a cryocatheter at a predetermined site in the vasculature of a patient, wherein the tip is substantially cylindrical-shaped and surrounds a chamber defining a longitudinal axis, said method comprising the steps of:

positioning a guidewire in the vasculature of the patient across the predetermined site;

providing a catheter body having a distal end, with said tip attached to said distal end of said catheter body, and a connector positioned at said tip, said connector being formed with a passageway for receiving said guidewire therethrough;

threading said guidewire through said passageway; and advancing said catheter body along said guidewire through the vasculature, to position said tip of said cryocatheter at the predetermined site;

providing a fluid source;

providing a hollow, tubular shaped supply line having a proximal end and a distal end, said supply line positioned inside said catheter body with said distal end of said supply line positioned in said chamber, and said proximal end of said supply line in fluid communication with said fluid source; and introducing a fluid from said fluid source into said chamber through said supply line to cool said tip.

13. A method as recited in claim 12 wherein said connector is an eyelet comprising:
   an annular shaped member, with said annular shaped member defining said passageway; and
   an extension arm having a first end and a second end, wherein said first end of said extension arm is positioned at said tip and said second end of said extension arm is affixed to said annular shaped member to project said annular shaped member radially outward from said tip to receive said guidewire.

14. A method as recited in claim 13 wherein said first end of said extension arm is formed into a ring, said method further comprising the steps of:
   providing a post having a first end and a second end with said first end of said post attached to said closed end of said tip to extend said post axially from said tip in a distal direction to receive said ring around said post; and
   providing a cap attached to said second end of said post for holding said connector on said tip to rotate said connector around said axis.

15. A method as recited in claim 12 wherein said catheter body is substantially cylindrical-shaped and has a wall surrounding a lumen, with said wall having an inner surface and an outer surface, wherein said passageway extends through said wall between said inner surface and said outer surface from a first opening to a second opening, and wherein said first opening and said second opening are located on said outer surface of said wall of said catheter body.

16. A method as recited in claim 15 wherein said passageway extends from said first opening to said second opening along a substantially straight path.

* * * * *

UNITED STATES PATENT AND TRADEMARK OFFICE
CERTIFICATE OF CORRECTION

PATENT NO. : 6,824,543 B2
DATED : November 30, 2004
INVENTOR(S) : David J. Lentz It is certified that error appears in the above-identified patent and that said Letters Patent is hereby corrected as shown below:

Column 7,
Line 51, delete "wail." insert -- wall. --

Signed and Sealed this

Nineteenth Day of April, 2005

JON W. DUDAS
*Director of the United States Patent and Trademark Office*